(12) United States Patent
Wahnschafft

(10) Patent No.: US 9,901,294 B2
(45) Date of Patent: Feb. 27, 2018

(54) DEVICE AND SYSTEM FOR THE PREVENTION OF AN INDIVIDUAL OPERATING A VEHICLE WHILE IMPAIRED

(71) Applicant: Kiara Wahnschafft, Winchester, MA (US)

(72) Inventor: Kiara Wahnschafft, Winchester, MA (US)

( * ) Notice: Subject to any disclaimer, the term of this patent is extended or adjusted under 35 U.S.C. 154(b) by 0 days.

(21) Appl. No.: 15/229,394

(22) Filed: Aug. 5, 2016

(65) Prior Publication Data

US 2017/0035332 A1 Feb. 9, 2017

Related U.S. Application Data

(60) Provisional application No. 62/201,121, filed on Aug. 5, 2015.

(51) Int. Cl.
| G08B 23/00 | (2006.01) |
| A61B 5/145 | (2006.01) |
| A45C 11/00 | (2006.01) |

(52) U.S. Cl.
CPC ......... *A61B 5/14546* (2013.01); *A45C 11/00* (2013.01); *A45C 2011/002* (2013.01)

(58) Field of Classification Search
CPC ............................. E05B 17/223; B60K 28/063
USPC ........................................................ 340/576
See application file for complete search history.

(56) References Cited

U.S. PATENT DOCUMENTS

| 2005/0053904 A1* | 3/2005 | Shephard | G09B 7/00 |
| | | | 434/236 |
| 2006/0182661 A1* | 8/2006 | Aquila | B60K 28/063 |
| | | | 422/84 |
| 2011/0252839 A1* | 10/2011 | Stevens | E05B 19/0005 |
| | | | 70/63 |
| 2011/0277537 A1* | 11/2011 | Tsuzuki | A61B 5/082 |
| | | | 73/23.3 |
| 2012/0112879 A1* | 5/2012 | Ekchian | A61B 5/117 |
| | | | 340/5.53 |
| 2013/0345593 A1* | 12/2013 | Burns | G06F 19/3431 |
| | | | 600/558 |

\* cited by examiner

*Primary Examiner* — Fabricio R Murillo Garcia
(74) *Attorney, Agent, or Firm* — Bay State IP, LLC

(57) ABSTRACT

The subject device and associated system relates generally to assessing impairment of an individual to determine whether to provide access to operate a motor vehicle, providing an ignition interlock that works without requiring modification in a motor vehicle and allowing an individual to start the vehicle only following measurement of blood alcohol content or following a series of cognitive tasks to determine the level of impairment. The systems and devices described herein relate incorporate a shielded case designed to disable communication between wireless car keys and the corresponding motor vehicles. This method of achieving an ignition interlock can be combined with a breathalyzer, or with a fingerprint alcohol sensor, or with cognitive tests running on a mobile computing device.

15 Claims, 8 Drawing Sheets

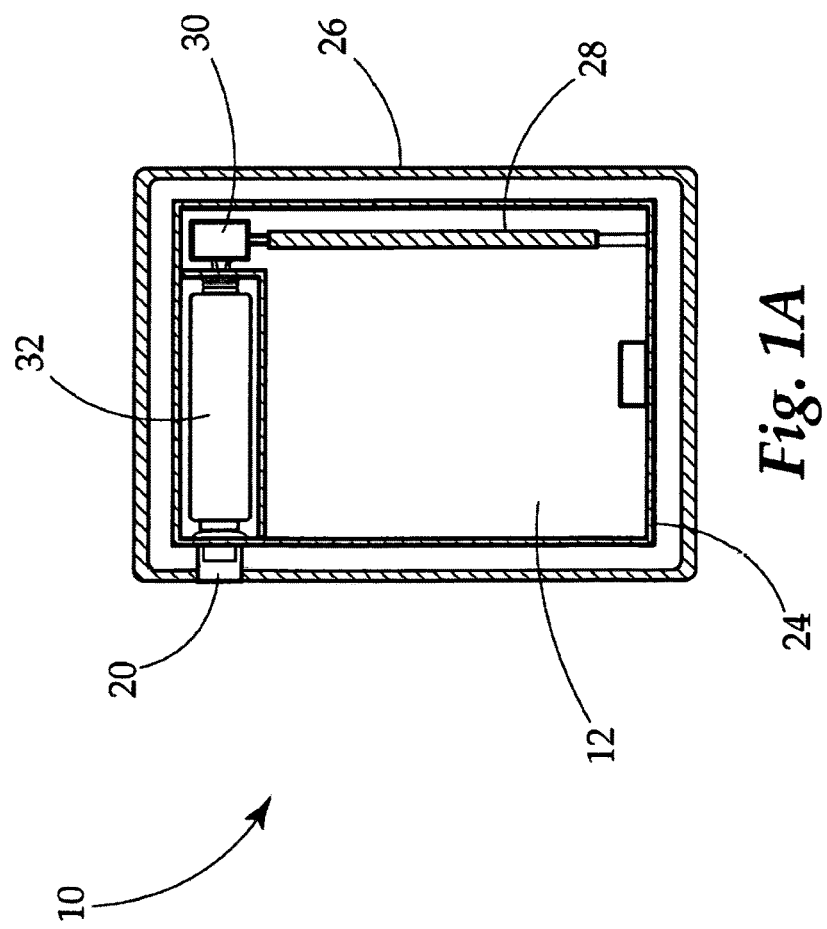

| | |
|---|---|
| 10 | Key Case |
| 20 | Socket |
| 22 | Computing Device |

DEVICE AND SYSTEM FOR THE PREVENTION OF AN INDIVIDUAL OPERATING A VEHICLE WHILE IMPAIRED

CROSS REFERENCE TO RELATED APPLICATION

This application claims priority to and takes the benefit of U.S. Provisional Application Ser. No. 62/201,121 filed on Aug. 5, 2015, the contents of which are herein incorporated by reference.

BACKGROUND OF THE INVENTION

Field of the Invention

The subject device and associated system relates generally to assessing impairment of an individual to determine whether to provide access to operate a motor vehicle, providing an ignition interlock that works without requiring modification in a motor vehicle and allowing an individual to start the motor vehicle only following measurement of blood alcohol content or following a series of cognitive tasks to determine the level of impairment.

Description of the Related Art

Driver fitness is typically considered a function of sensory, motor, and cognitive skills. The most common cause of impairments is the influence of alcohol. In most countries, the allowable level of blood alcohol is determined by law. In some countries it is zero; in the United States it is 0.08%, although lower level intoxication can result in result in a criminal offense in a number of states, and many states have lower level limits for younger operators. It is well documented that younger people, especially teen drivers, are prone to more risky behavior even at very low levels of blood alcohol levels. This phenomenon couples with a reduced performance in cognitive abilities caused by intoxication. Over the past decade, the number of fatal accidents recorded every year has not changed significantly any more, despite the introduction of new safety features in cars. Statistics show that drivers who are caught or get involved in an accident with elevated alcohol levels are likely to have driven many times in intoxicated condition before. Hence the biggest opportunity for further reducing the number of accidents is by focusing on technology that prevents impaired driving. With alcohol being the most common cause of impairment, it should be the first problem to be dealt with.

The most accurate measurement method for determining blood alcohol content involves drawing blood. Such an approach would be used only in extreme cases, for example after a serious accident.

The most established non-invasive technology for measuring the blood alcohol content is a breathalyzer. The breathalyzer technology is used by law enforcement authorities. Breathalyzer technology is available for built in applications in automobiles, where a car cannot be started when the breathalyzer detects a level of alcohol higher than the set limit. Built in breathalyzers are primarily used when required by a judge for operators with drunk driving convictions. This ignition interlock technology is expensive and requires customer installation.

The proposed invention makes it possible to incorporate a breathalyzer into a portable device which acts as an ignition interlock using just the car key provided by the automobile manufacturer.

Alternative non-invasive methods for measuring blood alcohol content have been previously proposed. It is possible to use an infrared scanner to analyze for alcohol in the blood through the skin. Numerous research publications support the conclusion that such sensors can correlate quite accurately with blood measurements and breathalyzer data, although there is a larger lag time for alcohol to show up in the perspiration, which is what the infrared sensors measure. There appear to be two key obstacles that have held back the deployment of infrared alcohol sensors for alcohol detection in a broader way with vehicle start interlocks. These are, a) it is difficult to prevent the alcohol sensor from being bypassed, e.g. the system has to make sure it is testing the operator's skin, and b) the systems that are being pursued require a complex installation process in the vehicles. Both of these challenges limit adoption of the alcohol sensor technology in commercial use in vehicles. In one embodiment of the proposed invention, the device and system provide an ignition interlock that does not require installation in an automobile, and the combination of a biometric fingerprint sensor and infrared alcohol sensor limit the possibility of manipulating the system.

Another approach for determining impairment is to use cognitive tests which can be made available on mobile devices. Cognitive tests have the advantage that they can reveal impairments due to causes other than alcohol consumption, such as exhaustion, drugs, or certain medical conditions. For this reason, it is desirable to make it possible to use methods and systems implementing cognitive tests on mobile devices such as smartphones, watches and tablet computers in conjunction with vehicle start interlocks, or at least with notifications of interested parties such as guardians or employers.

SUMMARY OF THE INVENTION

The device and system, as illustrated herein, is clearly not anticipated, rendered obvious, or even present in any of the prior art mechanisms, either alone or in any combination thereof. The versatile device and system allows for the assessment and prevention of an individual from operating a vehicle unless the individual is determined not to be impaired by the system. Thus the several embodiments of the mechanism are illustrated herein.

The system and device described herein is designed to provide an ignition interlock which prevents an operator from starting a vehicle unless the operator passes an impairment test.

While most prior art has focused on technology that gets built into automobiles in order to be able to effect an ignition interlock, the device proposed herein has the advantage that it focuses on the use of a key for a motor vehicle. In practice, most vehicles require a key without which an operator cannot start the vehicle. The device proposed herein is designed such that the key is not usable unless the operator passes the impairment test.

In a preferred embodiment, the system and device incorporate a breathalyzer. In another preferred embodiment, the system and device utilizes infrared sensor technology for alcohol detection, combined with fingerprint identification. In another embodiment, the systems and devices utilize cognitive tests for detection of a broader range of impairments including those caused by alcohol, drugs, medical conditions, or exhaustion.

There has thus been outlined, rather broadly, the more important features of a device and system providing an ignition interlock subject to the assessment of an individual's impairment in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

These and other features, aspects and advantages of the present invention will become better understood with reference to the following description, appended claims and accompanying drawings, in which:

FIG. 1A is a perspective cross-sectional view of a key case device for housing a wireless key and restricting its communication with a motor vehicle using metal shielding and known in the art circuitry to control the ability to start a motor vehicle subject to assessing an individual's level of impairment.

DETAILED DESCRIPTION OF THE SEVERAL EMBODIMENTS

Figure 1B:
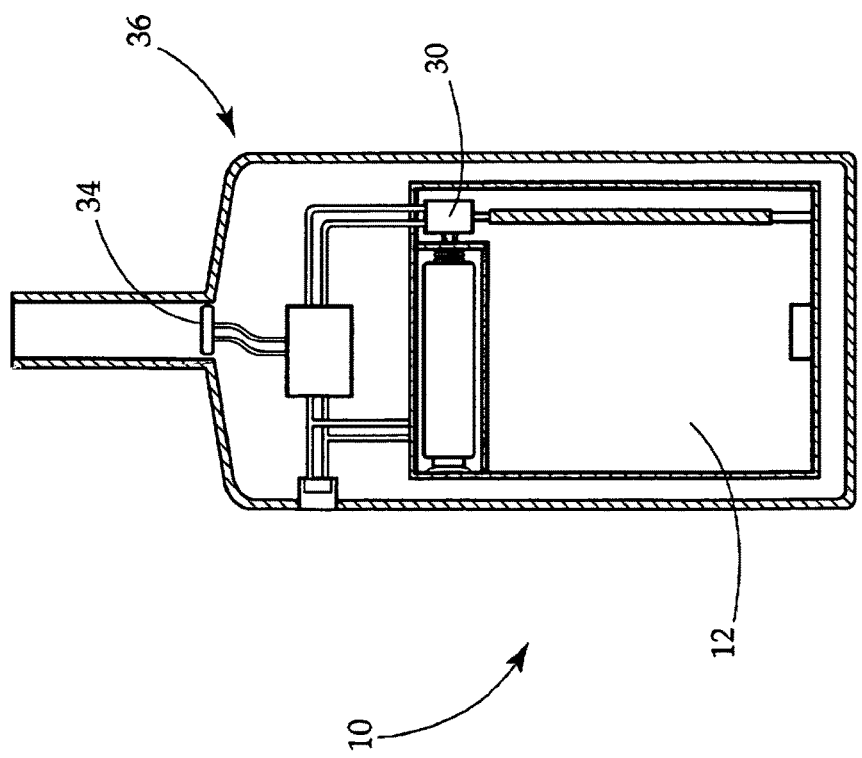
FIG. 1B is a perspective cross-section view illustrating one embodiment of the key case device incorporating a breathalyzer using a vapor analysis alcohol sensor.

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

The systems and devices described herein may hence be used in existing vehicles without requiring modifications in the vehicle; as such, the instant device and system is designed to work with existing wireless keys. These key fobs emit a signal which, when close enough to the vehicle, results in unlocking the ignition so it can be started by pushing a button in the car. The systems and devices described herein all incorporate a mechanism that controls the communication between the wireless key and the motor vehicle using movable shielding. The key case is designed to accept a wireless car key which gets locked up in the case. An individual using the key case does not have the ability to open it. The key case can control whether or not the wireless signal of the key communicates with the associated motor vehicle.

Primary application areas are ignition interlocks for vehicles used for transport of people and goods (buses, trucks, taxicabs, privately operated commercial transport vehicles, etc.) as well as regular passenger automobiles or motorcycles, especially when used by teenagers where the alcohol threshold should be set even lower than the legal limit allowed for adult operators. However, the proposed systems and devices may readily be put to use for other types of equipment, such as heavy machinery and even tools that present elevated dangers to the operator and others when the operator is impaired.

FIG. 1A illustrates a cross-sectional schematic view of one embodiment of a key case 10, for preferably housing a wireless motor vehicle key fob (not shown), wherein the key case 10 further includes a plurality of metal shielding 24 that surrounds the housing 12 for the key case 10 to prevent a key from transmitting a signal to a motor vehicle. In one embodiment, the housing 12 works itself is a lockable chamber, and in other embodiments the housing works in conjunction with the lockable cover 14. Additionally, an outer casing 26 may be provided to surround the metal shielding 24. In a preferred embodiment, a portion of the metal shielding 24 is configured as a movable metal shield gate 28 that may be controlled by a motor unit 30, wherein the gate 28 is opened to allow the signal transmitted from the enclosed key to reach the ignition control device in the motor vehicle upon an individual passing a blood alcohol test or a series of impairment tests. In other embodiments, the key case 10 further includes a battery 32 to power the motor unit 30, wherein the battery 32 may recharged via the socket 20.

FIG. 1B illustrates an alternate embodiment of the key case 10, wherein the key case 10 further includes an alcohol sensor 34 as part of a breathalyzer utilized to measure the level of alcohol in an individual attempting to start a motor vehicle using the key in case 10. Furthermore, the key case 10 may include a processing unit 36, which may be programmed to set the acceptable alcohol level and compare it with the measurement of the individual. If the measurement is below the acceptable threshold value (which may be set to a custom value via a software program running on a connected computing device 22), the processing unit 36 will output a signal to the motor unit 30 to open the movable metal shield gate 28. In alternate embodiments, the processing unit 36 may include a timer which closes the metal shield gate 28 after a predetermined time period. In this embodiment, the processing unit 36 may include an integrated circuit and accompanying microprocessor to receive inputs from the fingerprint sensor 16 and alcohol sensor 34 to analyze against stored values, preferably in a user database.

Figure 1C:
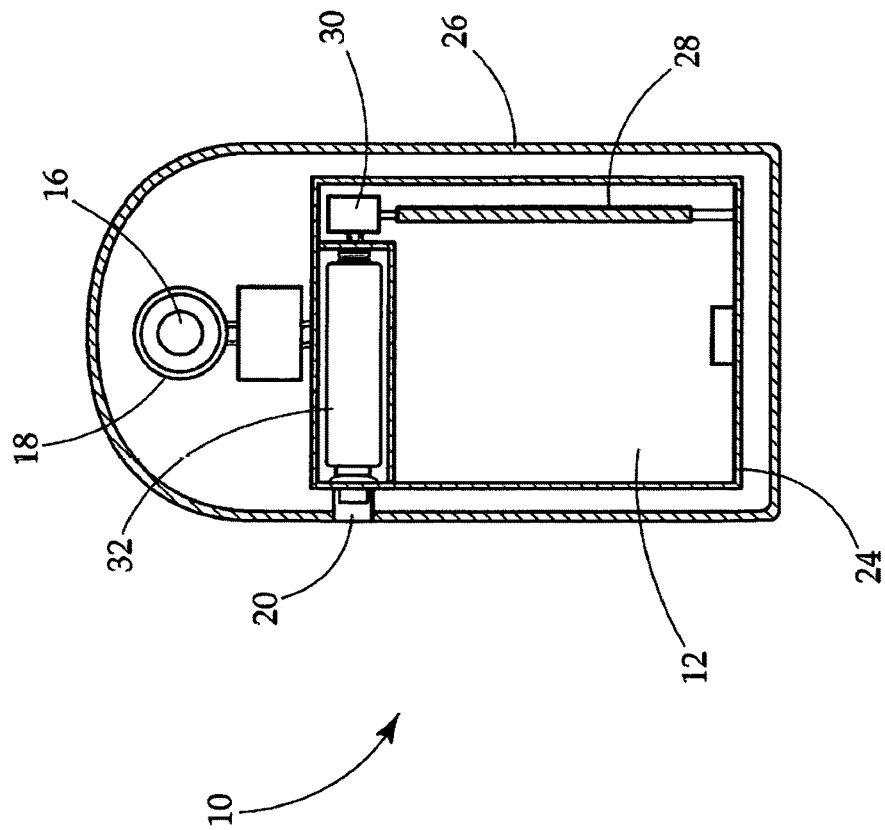
FIG. 1C is a perspective cross section of one embodiment of the key case device for incorporating a biometric fingerprint sensor and an infrared scanner for blood alcohol measurement.

FIG. 1C illustrates one embodiment of a key case 10 for preferably housing a motor vehicle key fob (not shown), wherein the key case 10 further includes a fingerprint sensor for biometric identity verification 16 coupled with an infrared sensor for blood alcohol content measurement through the skin 18, thereby serving the dual purpose of verifying that the individual attempting to enable the enclosed key to communicate with the automobile is the one authorized to access the key AND allowing for the detection of any presence of alcohol in the system of the individual. In alternate embodiments, the key case 10 may further include a socket 20 (i.e. USB port or other similar means) to enable electronic and data communication between the key case 10 and a computing device 22 (shown in FIG. 2A). In yet another alternate embodiment, a lip print scanner may be incorporated within the key case 10 for identification purposes and/or interchanged with the fingerprint sensor 16 to verify that the individual looking for access to start a motor vehicle is the proper individual.

Figure 2A:
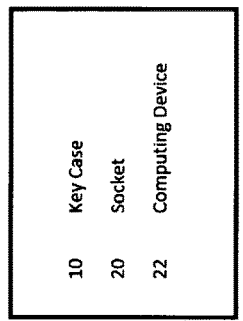
FIG. 2A is one embodiment of the key case device in electronic and data communication with a corresponding computing device.
Figure 2A:
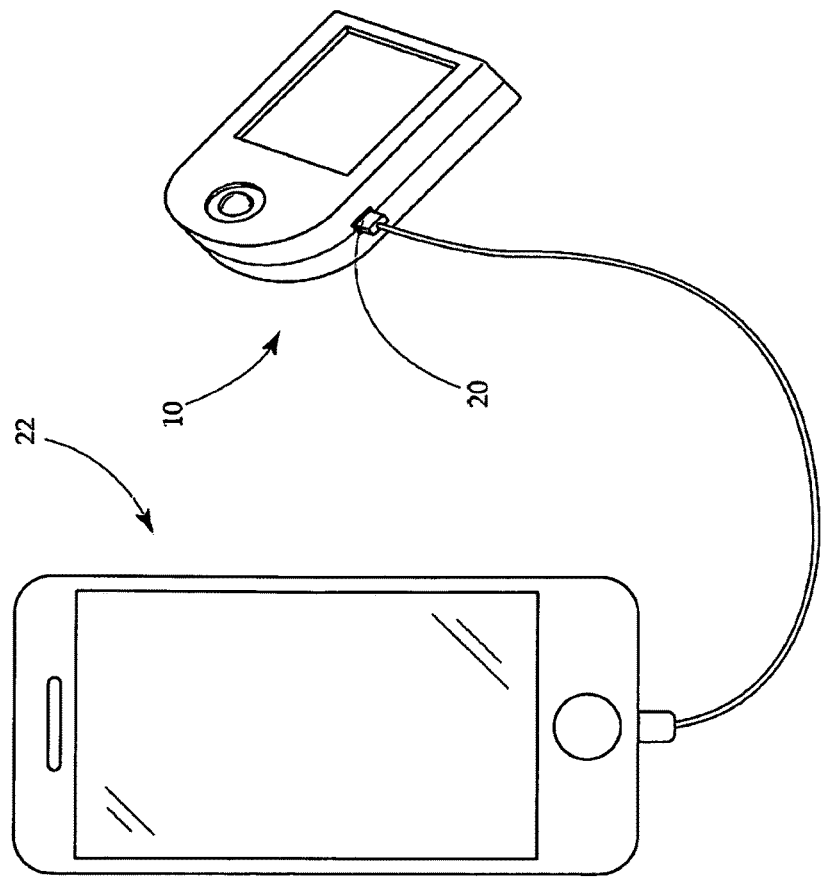

FIG. 2A illustrates one embodiment of a system diagram, wherein the key case 10 may be utilized in conjunction with a corresponding computing device 22. In this embodiment, the key case 10 and the computing device 22 are in data and electronic communication with each through known in the art connection means via the socket 20 of the key case 10 and a corresponding port in the computing device 22. Herein, illustrated in this embodiment, the key case 10 is attached to a smart phone 22; the key case 10 may also be attached to other computing devices. Some examples of computing devices include: a computer, desktop, laptop, tablet, mobile device, smart phone, etc. so that the key case 10 may be programmed appropriately in accordance with a user's preferences.

Figure 2B:
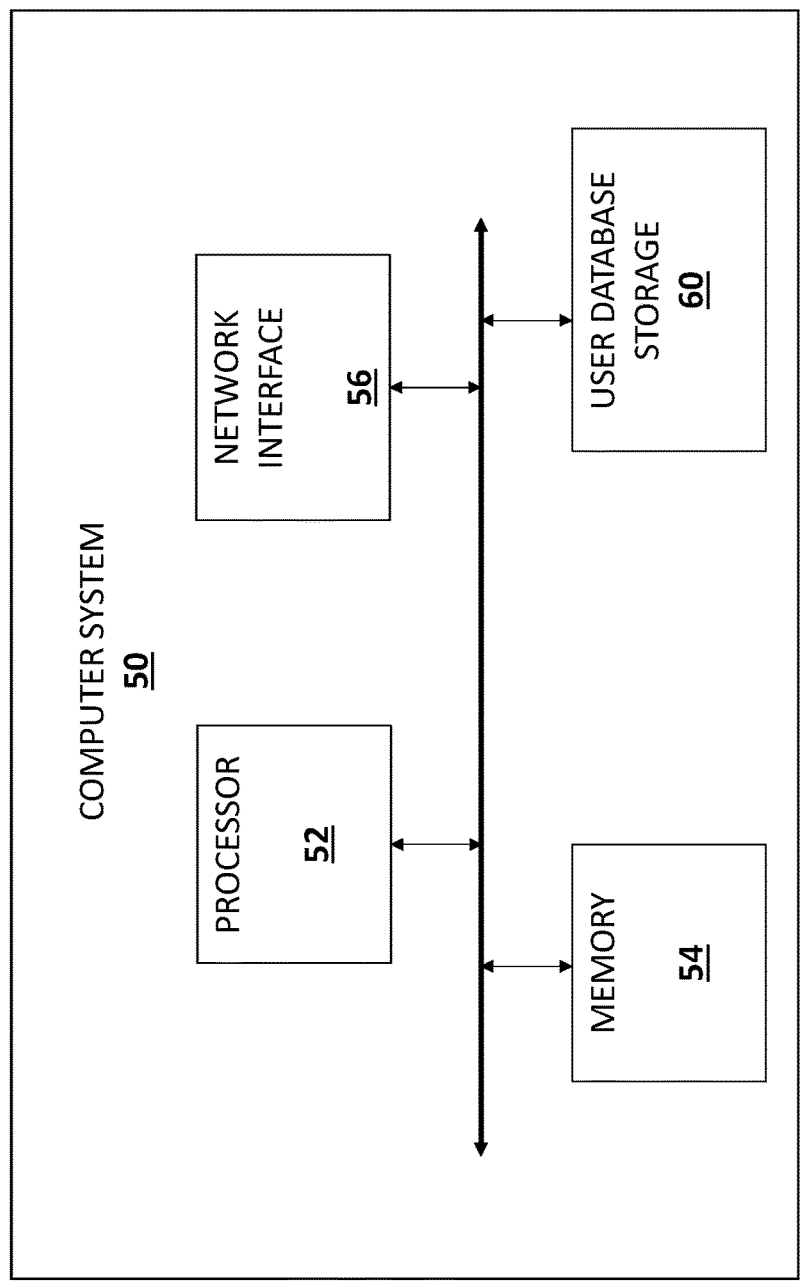
FIG. 2B is an exemplary computing environment for a computing device used in conjunction with the key case device.

The systems and methods disclosed herein may be implemented using one or more computer systems, such as the exemplary embodiment of a computer system 50 shown in FIG. 2B. The computer system 50 may represent, for example, computing or processing capabilities found within desktop, laptop, and notebook computers, handheld computing devices (PDAs, smart phones, cell phones, palmtops, etc.), mainframes, supercomputers, workstations or servers, or any other type of special or general purpose computing devices as may be desirable or appropriate for a given application or environment. As shown, the computer system 50 may include one or more processors or processing devices, such as processor 52 which can control the operation of the computer system 50. The processor(s) 52 can include any type of microprocessor or central processing unit (CPU). Further, the processor 52 might be implemented using a general-purpose or special-purpose processing engine such as a microprocessor, controller or other control logic.

Computing system 50 might also include one or more memory modules, referred to as main memory 54. For example, preferably random access memory (RAM) or other dynamic memory, might be used for storing information and instructions to be executed by the processor 52. Main memory 54 might also be used for storing temporary variables or other intermediate information during execution of instructions to be executed by processor 52. The main memory 54 may also store data acquired from one or more users, storage devices, and/or databases. The computer system 50 can also include one or more network interface(s) 56, and one or more storage device(s).

The network interface(s) 56 can enable the computer system 50 to communicate with remote devices (e.g., other computer systems) over a network, and can be, for example, remote desktop connection interfaces, Ethernet adapters, and/or other local area network (LAN) adapters. Additionally, the computing system 50 may include a plurality of user databases 60 which may include any conventional medium for storing data in a non-volatile and/or non-transient manner. The databases 60 can thus hold data and/or instructions in a persistent state (i.e., the value is retained despite interruption of power to the computer system 50).

Exemplary computer systems include conventional desktop computers, workstations, minicomputers, laptop computers, tablet computers, PDAs, mobile phones, and the like. Although an exemplary computer system is depicted and described herein, it will be appreciated that this is for sake of generality and convenience. In other embodiments, the computer system may differ in architecture and operation from that shown and described here.

Figure 3:
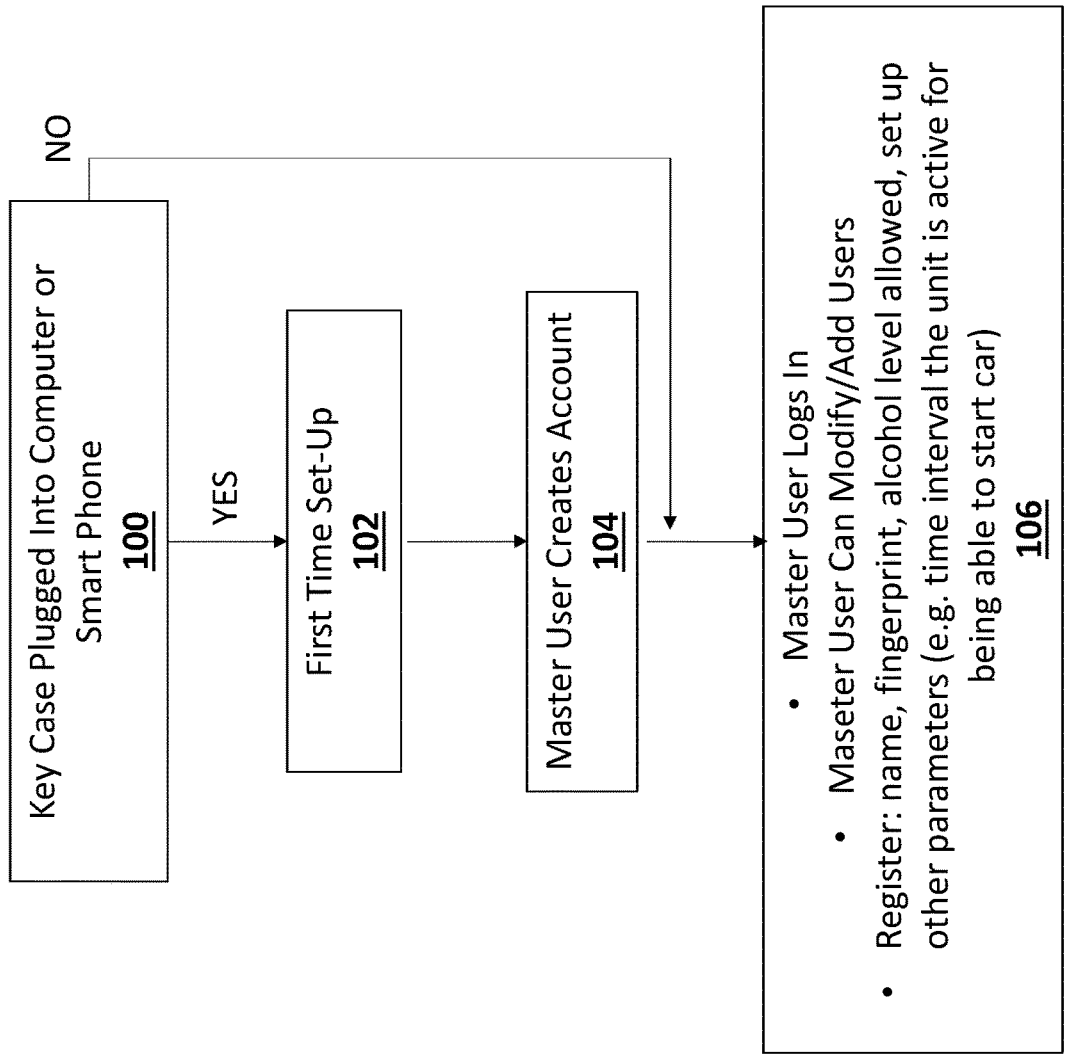
FIG. 3 is a flow diagram illustrating one embodiment of a series of steps for setting up an alcohol sensor in the device for an individual's use to determine a level of impairment.

FIG. 3 is a flow diagram illustrating one embodiment of a series of steps for setting up an alcohol sensor in the key case device 10 for a user to determine a level of impairment. Initially, at step 100, the key case 10 is connected to the computing device 22. At step 102, when the connection is for an initial set up, a user proceeds to step 104, wherein the user creates a master user account 104. Following the creation of a master user account, at step 106, the user may register his name, fingerprint(s), alcohol level allowed, set up certain parameters (e.g. time interval the unit is active for being able to start a car), etc. The master user may have the ability to program the key case for different potential operators. After a user has set up his initial account for the first time, any time he connects the key case to the computing system, he may proceed directly to step 106, wherein he can modify the account, add new user accounts, edit information, delete accounts, etc. The master user can then add or modify information for allowed operators. The master user can have users add their fingerprints and set the maximum level of blood alcohol content at which the key will allow an operator to start the vehicle.

Figure 4:
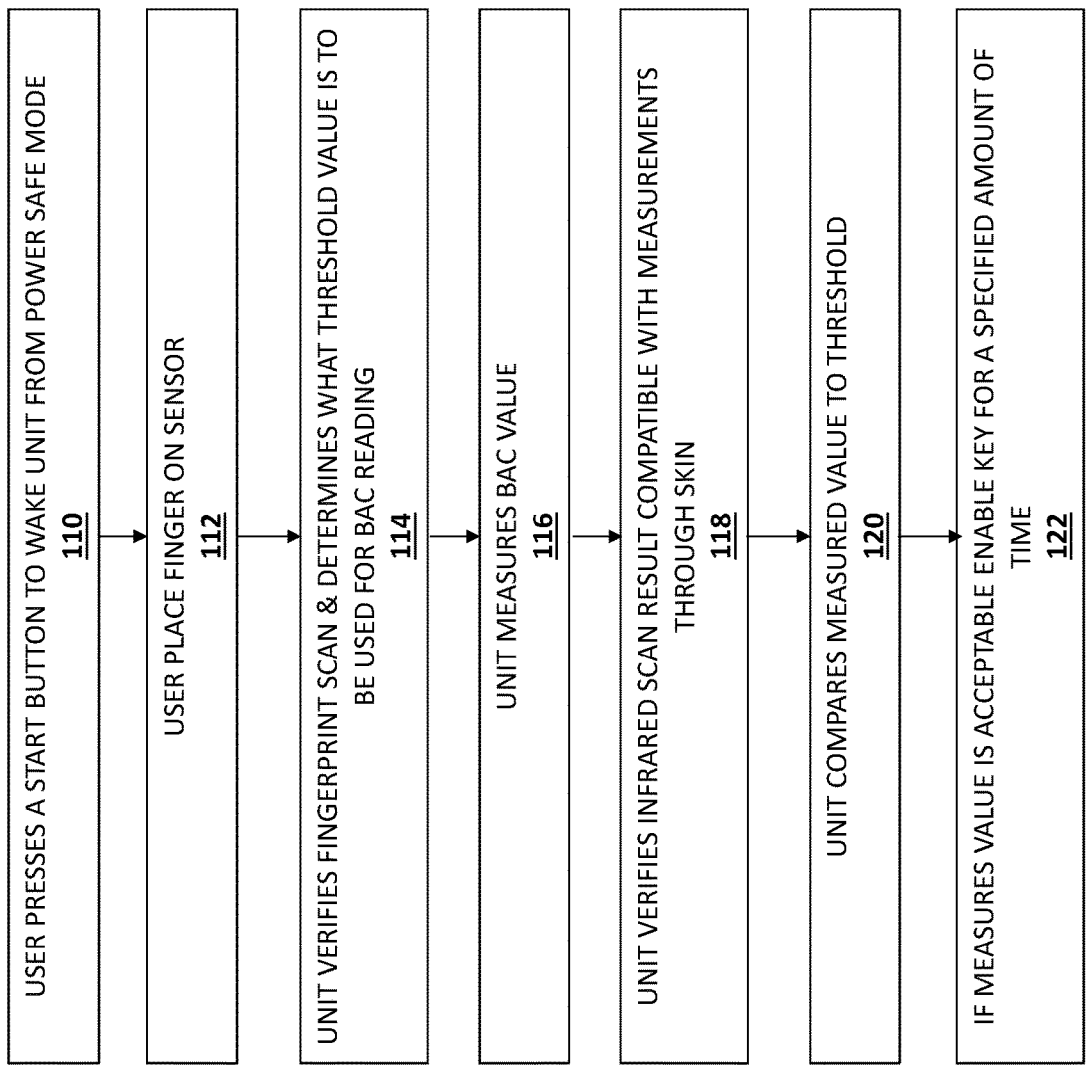
FIG. 4 is a flow diagram illustrating one embodiment for the operation of the device to determine the level of impairment of an individual and whether to allow access to a motor vehicle key housed within the device.

FIG. 4 is a flow diagram illustrating one embodiment of a series of steps for utilizing the alcohol sensor 34 of the key case 10. Initially, at step 110 in one embodiment, a user presses or pushes a start button to wake the key case 10 from a power safe mode. Then, at step 112 the user places his or her finger on the fingerprint sensor 16 in a similar fashion as to when they their finger into the account during initial set-up. Subsequently, at step 114, the key case 10 device verifies the fingerprint scan and determines the threshold value of the individual to be used for the blood alcohol (BAC) reading based on the initial inputs during step up as described in FIG. 3. Then, at step 116, the key case 10 measures the user's BAC value through the alcohol sensor 34 or the infrared sensor 18 depending on the embodiment. At step, 118 the key case 10 verifies result compatible with measurements through the skin utilizing the infrared system. At step 120, the key case 10 compares the user's measured value to the user's set threshold level. After the key case 10 measures the user's value and compares it to the user's threshold value, at step 122, if the user's measured value is acceptable then the key case 10 unlocks and the key is enabled for a specified amount of time to be utilized by the user.

The described device is just one of many possible implementations of the idea of creating a key with a fingerprint sensor and an alcohol touch sensor. A logical extension of the concept would be to incorporate the fingerprint and alcohol sensors into devices that do not require the encasement of a key fob. It would be possible for automobile manufacturers and the suppliers of the key fob technology to use the concept described herein to incorporate the fingerprint and alcohol sensing technology into a smaller wireless key fob which can be programmable as described above.

Integrating Alcohol Test and Wireless Key Functionality with Mobile Devices

Another extension of the proposed concept of combining alcohol sensors and fingerprint sensors with wireless key functionality would be to integrate these functions with mobile computing devices, such as smartphones, watches or tablet computers.

Figure 5:
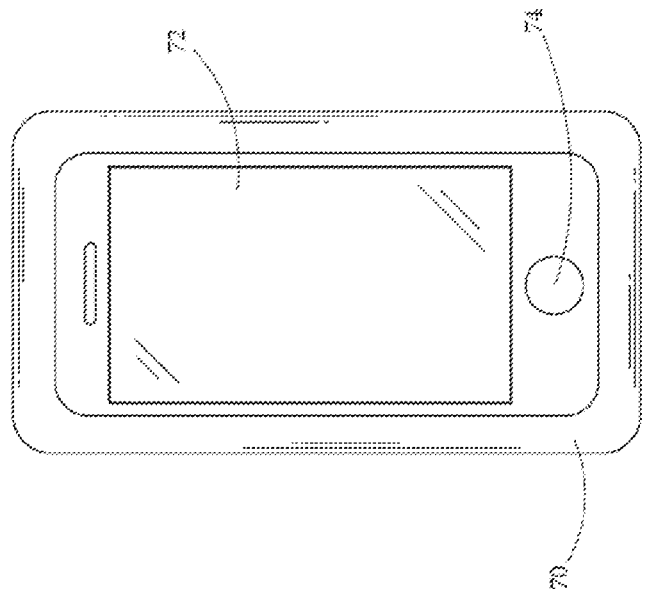
FIG. 5 is a perspective view of an alternate embodiment, wherein a mobile computing device is utilized in connection with the device housing the motor vehicle key to administer a series of impairment tests.

FIG. 5 illustrates an additional embodiment of the device wherein the system is utilized by a smart phone or mobile phone protective case 70. The mobile phone protective case 50 can house the infrared sensor and the wireless key functionality, while the smartphone 72 provides the fingerprint identification technology 74 as well as the software and computing processing unit which determines if the vehicle start interlock is released.

Combining the impairment test with a mobile computing device offers other benefits. For example it is readily possible to communicate the results of an operator taking an impairment test to an affected party, like a parent, guardian, or employer. Moreover, mobile computing devices such as smartphones offer GPS tracking capability, so it is easily possible to track the operator's location. This feature could be a great benefit for commercial transport as well as for concerned parents of teenage drivers.

Cognitive Tests and Vehicle Interlocks

In order to ensure that an operator is within prescribed limits of alcohol intake it is required to measure blood alcohol directly or indirectly as described above. However, there are other sources of impairment which cannot be measured that way. In certain aspects, the system and devices described below assess possible brain impairment in a human not limited to impairment caused by alcohol intake. In such aspects, the system comprises a database configured to store a performance threshold associated with limits for safe operation of a vehicle and a processor configured to present one or more assessment tasks to a first user, receive input from the first user in response to the one or more assessment tasks, and score the input received in response to the one or more assessment tasks. The one or more assessment tasks may include questions for the first user to answer, actions for the first user to perform, or other suitable tasks. The processor is further configured to output a signal which determines if the operator is allowed to start a vehicle.

In some implementations, the possible impairment is alcohol intoxication. However, the key advantage of using cognitive tests is that they can reveal impairments caused by other issues such as drugs, exhaustion, or medical conditions.

In some implementations, one or more elements of the system may be implemented on a cloud computing device.

Figure 6:
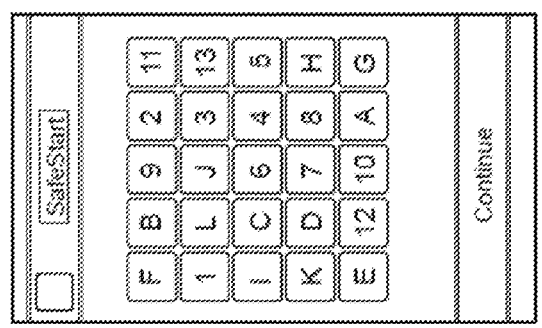
FIG. 6 is an exemplary screenshot of a Trail Making Test screen, an example of a cognitive test that assesses speed of reaction and concentration, according to an illustrative implementation.

In some implementations, the cognitive evaluation may include one or more problem-solving tasks (e.g., a Tower of Hanoi task, a mathematical processing task, and a logical reasoning task), one or more attention tasks (e.g., a running memory continuous performance task, and a Stroop test), one or more working memory tasks (e.g., a digit span test, a code substitution task, and a digit set comparison task), one or more reaction time tasks (e.g., a two-choice reaction time test, a four-choice reaction time test, and a procedural reaction time test), one or more visuospatial tasks, as seen in FIG. 6 (e.g., a Trail Making Test, a spatial processing task, and a tracking task), one or more non-cognitive tasks (e.g., a balance task), or other suitable tasks, and the processor may be further configured to randomly generate one or more of such tasks. Specifically, FIG. 6 illustrates an example of reaction and concentration test 94.

In some implementations, the processor is further configured to output an indicator representative of the comparison to acceptable threshold values to a second user, who may be a legal guardian, an employer of the operator, or some other suitable second party. In some such implementations, the processor is further configured to receive feedback from the second user responding to the indicator. As an illustrative example of such an implementation, a vehicle dispatcher may determine that a bus operator should not be driving even though his or her blood alcohol level may not be above the legal limit.

In some implementations, the processor is further configured to present the one or more assessment tasks for completion within a predetermined period of response time. The predetermined period of response time may be thirty seconds, or fifteen seconds, or some other suitable period of response time.

Figure 7:
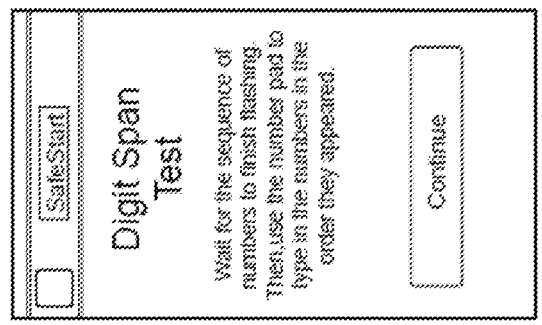
FIG. 7 is a screenshot of a digit span test screen, a fast test of memory, according to an illustrative implementation.

In some implementations, the one or more assessment tasks include one or more problem-solving tasks (e.g., a Tower of Hanoi task, a mathematical processing task, and a logical reasoning task), one or more attention tasks (e.g., a running memory continuous performance task, and a Stroop test), one or more working memory tasks, as shown in FIG. 7 (e.g., a digit span test, a code substitution task, and a digit set comparison task), one or more reaction time tasks (e.g., a two-choice reaction time test, a four choice reaction time test, and a procedural reaction time test), one or more visuospatial tasks (e.g., a Trail Making Test, a spatial processing task, and a tracking task), non-cognitive tasks (e.g., a balance task), or other suitable tasks, and the processor may be further configured to randomly generate one or more of such tasks. Herein, FIG. 7 illustrates instructions for a memory performance test known as Digit Span Test 96.

In some implementations, the processor is further configured to receive sensor data associated with the user, wherein the input score is based on the sensor data. Such data may include accelerometer data, touchscreen data, heart rate data, or other suitable data. Balance tasks would fall into this category.

In some implementations, the processor is further configured to identify a location of and/or contact to make alternate transport arrangements for the first user.

In certain aspects, the computer-implemented method described herein assesses possible temporary brain impairment in a human. In such aspects, the method comprises presenting one or more assessment tasks to administer to a first user, receiving input from the first user in response to the one or more assessment tasks, scoring the input received in response to the one or more assessment tasks, and identifying whether the first user met a performance threshold associated with safe operation. The one or more assessment tasks may include questions for the first user to answer, actions for the first user to perform, or other suitable tasks. The method outputs an indicator representative of a comparison of the input score to the performance threshold. This output can affect a vehicle start interlock by unlocking the key, as described above. The output may also be a notification transmitted to a second user, for example a guardian or a representative of the operator's employer. In some implementations, the possible brain impairment is alcohol or drug intoxication.

It should be understood that various alternatives to the embodiments of the disclosure described herein may be employed in practicing the disclosure. Elements of an implementation of the systems and devices described herein may be independently implemented or combined with other implementations. It is intended that the following claims define the scope of the disclosure and that systems, methods and devices within the scope of these claims and their equivalents be covered thereby.

What is claimed is:

1. An impairment measurement system configured to assess the impairment of an individual prior to operating a vehicle, the impairment measurement system comprising:
    a key case, preferably for housing a wireless motor vehicle key fob, wherein the key case further comprises:
    a housing, wherein the housing surrounds the key case and works in conjunction with a lockable cover;
    a plurality of metal shielding, wherein the metal shielding surrounds the housing for the key case;
    an outer casing, wherein the outer casing surrounds the metal shielding;
    a fingerprint sensor for biometric identity verification;
    an alcohol sensor;
    an infrared sensor for alcohol content measurement through a user's skin; and
    a processor unit in data communication with a user database;
    wherein the processor unit is configured to:
        identify at least one individual through the fingerprint sensor on the key case;
        measure a level of blood alcohol content in the individual through the alcohol sensor on the key case;
        compare the measured blood alcohol content to a threshold value of the individual stored in the user database;
        generate an output by the processor unit based on a comparison of the measured value to the threshold value;
        wherein the output represents an access approval or an access denial to the wireless motor vehicle key fob.

2. The impairment measurement system of claim 1, wherein the processor unit is in data communication with at least one user database.

3. The impairment measurement system of claim 2, wherein the at least one user database stores at least one threshold value of at least one individual stored in the user database.

4. The impairment measurement system of claim 1, wherein the impairment measurement system presents an individual with at least one cognitive impairment task to perform in order to access the wireless motor vehicle key fob.

5. The impairment measurement system of claim 4, wherein the at least one cognitive impairment task is a Trail Making Test.

6. The impairment measurement system of claim 4, wherein the at least one cognitive impairment task is a balance test.

7. The impairment measurement system of claim 4, wherein the at least one cognitive impairment task is a digit span memory test.

8. The impairment measurement system of claim 4, wherein the at least one cognitive impairment task is presented when the individual wants to start a motor vehicle.

9. The impairment measurement system of claim 4, wherein the at least one cognitive impairment task is configured to present the at least one cognitive impairment task within a predetermined period of response time.

10. The impairment measurement system of claim 4, wherein the processor unit is configured to automatically arrange an alternate transportation for the at least one individual who fails the at least one cognitive impairment task.

11. The impairment measurement system of claim 1, wherein the key case further comprises:
    a lip print scanner, wherein the lip print scanner is incorporated within the key case for identification purposes.

12. The impairment measurement system of claim 1, wherein the processor unit is further configured to:
    present the individual with at least one cognitive impairment task;
    measure a level of cognitive impairment through the least one cognitive impairment task;
    compare the level of cognitive impairment to a cognitive threshold value of the individual stored in the user database;
    generate an output by the processing unit based on a comparison of the measured level of cognitive impairment value to the cognitive threshold value.

13. The impairment measurement system of claim 12, wherein the processor unit is further configured to:
    generate an output notification to a second individual when the measured level of cognitive impairment value exceeds the cognitive threshold value.

14. The impairment measurement system of claim 13, wherein the second individual is a guardian.

15. The impairment measurement system of claim 13, wherein the second individual is an employer of the at least one individual.

* * * * *